US011185612B2

(12) United States Patent
Borges et al.

(10) Patent No.: US 11,185,612 B2
(45) Date of Patent: Nov. 30, 2021

(54) FABRICATION OF PCU/UHMWPE POLYMERIC BLENDS AND 3D PRINTING USING THE SAME

(71) Applicant: BOARD OF TRUSTEES OF THE UNIVERSITY OF ARKANSAS, Fayetteville, AR (US)

(72) Inventors: Raissa Araujo Borges, Memphis, TN (US); Min Zou, Fayetteville, AR (US)

(73) Assignee: Board Of Trustees Of The University Of Arkansas, Fayetteville, AR (US)

( * ) Notice: Subject to any disclaimer, the term of this patent is extended or adjusted under 35 U.S.C. 154(b) by 367 days.

(21) Appl. No.: 16/273,115

(22) Filed: Feb. 11, 2019

(65) Prior Publication Data
US 2019/0247544 A1 Aug. 15, 2019

Related U.S. Application Data
(60) Provisional application No. 62/628,746, filed on Feb. 9, 2018.

(51) Int. Cl.
A61L 27/50 (2006.01)
A61F 2/30 (2006.01)
A61L 27/18 (2006.01)
B33Y 10/00 (2015.01)
B33Y 70/00 (2020.01)
B29C 64/118 (2017.01)
A61L 27/26 (2006.01)
B29L 31/00 (2006.01)
(Continued)

(52) U.S. Cl.
CPC .......... *A61L 27/50* (2013.01); *A61F 2/30756* (2013.01); *A61L 27/18* (2013.01); *A61L 27/26* (2013.01); *B29C 64/118* (2017.08); *B33Y 10/00* (2014.12); *B33Y 70/00* (2014.12); *A61F 2002/30985* (2013.01); *A61L 2400/10* (2013.01); *B29K 2069/00* (2013.01); *B29L 2031/753* (2013.01); *B33Y 80/00* (2014.12)

(58) Field of Classification Search
CPC .......... A61L 27/50; A61L 27/26; A61L 27/18; A61L 2400/10; B29C 64/118; B29L 2031/753; B29K 2069/00; B33Y 80/00; B33Y 10/00; B33Y 70/00; D01F 6/46; D01F 6/94; A61F 2/3094; A61F 2/30756; A61F 2002/30985
See application file for complete search history.

(56) References Cited

U.S. PATENT DOCUMENTS

| 5,738,817 A * | 4/1998 | Danforth ................ B33Y 10/00 264/603 |
| 2015/0231302 A1* | 8/2015 | Duvall .................... A61L 27/18 424/93.7 |

(Continued)

Primary Examiner — Nahida Sultana
(74) Attorney, Agent, or Firm — Keith A. Vogt; Keith A. Vogt, Ltd.

(57) ABSTRACT

The present invention relates to methods of fabricating PCU/UHMWPE blended filaments and medical implantable structures using 3D printing of polymeric material, such as PCU/UHMWPE blend structures. The 3D printer dispenses said polymeric material in a layer-by-layer manner to create said medical implant. Polymeric material is dispensed at up to 100% infill. In one embodiment, the layer-by-layer dispensing is at a reduced speed for the bottom and top 1 to 10 layers.

15 Claims, 9 Drawing Sheets

(51) Int. Cl.
_B29K 69/00_ (2006.01)
_B33Y 80/00_ (2015.01)

(56) References Cited

U.S. PATENT DOCUMENTS

2016/0114077 A1* 4/2016 Song .................... A61F 2/28
  623/23.51
2017/0119924 A1* 5/2017 Guelcher .............. A61L 27/425
2021/0130608 A1* 5/2021 Gentsch ................... C08J 3/14

* cited by examiner

FABRICATION OF PCU/UHMWPE POLYMERIC BLENDS AND 3D PRINTING USING THE SAME

RELATED APPLICATIONS

This application claims priority to U.S. Provisional Application No. 62/628,746 filed on Feb. 9, 2018, which is hereby incorporated in its entirety.

STATEMENT REGARDING FEDERALLY SPONSORED RESEARCH & DEVELOPMENT

This invention was made with government support by the National Science Foundation under Grant Number OIA-1457888 and the Arkansas Biosciences Institute. The corresponding campus cost center numbers are 0402 36344-21-1601, 0402 36348-21-1601, 0402 36344-21-1701, 0402 36348-21-1701, and 0402-27504-21-0175, respectively. The government has certain rights in the invention.

INCORPORATION BY REFERENCE OF MATERIAL SUBMITTED ON A COMPACT DISC

Not applicable.

BACKGROUND OF THE INVENTION

According to the American Physical Therapy Association, around 700,000 Americans undergo knee surgery due to a meniscus injury every year. The meniscus, which is the cartilage cushion located between the tibia and the femur, plays a vital role in the functioning and protection of the knee joints by dispersing contact pressure and lowering coefficient of friction. It also contributes to the joint stability and force transmission and provides lubrication. However, the most common causes of knee surgeries are meniscus-related. When injured, the patient may have the damaged part removed, but that causes changes in the cartilage load distribution, which leads to degenerative arthritis.

A few options exist for partial meniscus repair and meniscus allograft transplantations, as well as total knee joint implants, but no artificial total meniscus replacement alternative was commercially available until the last decade. Ultra-high molecular weight polyethylene (UHMWPE) is a common material for polymeric components of artificial knee joints. Although cross-linked UHMWPE has excellent wear resistance, it can undergo oxidation in the presence of lipids in the body fluid. On the other hand, Polycarbonate urethane (PCU) has emerged as one of the best polymeric materials for joint application, combining wear and corrosion resistance, and mechanical stability. The first anatomically-shaped synthetic total meniscus implant, NUsurface® fabricated by Active Implants (Memphis, Tenn.), has been under clinical trials in the U.S. and has already been approved in some parts of Europe. The molded NUSurface® implant is made of a PCU (Bionate 80A) embedded with polyethylene-based fibers (Dyneema Purity®), resulting in a composite structure that combines the flexibility of PCU to distribute articular pressure and the load bearing capability of the UHMWPE reinforcement fibers. The solid nature of the molded implants, however, may impair the joint's ability to permit its natural lubrication mechanism to occur.

As a natural synovial joint, the lubrication in the knee is enabled by a fluid film that separates the two articulating surfaces. That unique tribological system has been explained by several lubrication mechanisms, which are mainly described by a combination of full fluid film lubrication, elastohydrodynamic lubrication (EHL), and micro-elastohydrodynamic lubrication (EHL). Furthermore, "weeping" lubrication happens when the joint is under dynamic load: the porous, natural meniscus absorbs interstitial synovial fluid with de-pressurization, and releases it upon loading, contributing to keeping the opposed surfaces apart. All those described mechanisms provide an extremely low coefficient of friction (COF), ranging from 0.002 to 0.04 and excellent wear resistance. As opposed to a native meniscus, a molded artificial meniscus implant, such as NUSurface®, has no porosity and is, consequently, unable to contribute to the joint lubrication through the "weeping" mechanism. Therefore, once it is implanted, the artificial meniscus can only maintain boundary lubrication on its surface by synovial fluid adsorption.

To mimic the optimal frictional and wear properties in a native meniscus, it is critical to include lubrication strategies along with bulk mechanical property considerations into the design and development of artificial cartilages.

BRIEF SUMMARY OF THE INVENTION

In one embodiment, the present invention relates to methods of fabrication implantable structures fabricated by methods using the 3D printing of PCU/UHMWPE blend structures. The 3D-printed implantable structures have sufficient porosity to retain lubricants thus enabling synovial joint's "weeping" lubrication mechanism to occur. 3D printing also adds the design freedom of making patient-specific implants and eliminates the need of fabricating a tailored implant mold for each patient.

In another embodiment, the present invention relates to the fabrication of PCU/UHMWPE blended filaments and 3D printing of the polymeric blended filaments by fused deposition modeling (FDM). PCU and UHMWPE are biocompatible polymers and have been used mainly in molded artificial articulating joints. UHMWPE is not suitable for extrusion-based processes due to its nearly zero melt-flow index. The present inventions fabricate PCU/UHMWPE blended filaments and 3D print them into a desired structure. The 3D printing fabrication process provides the necessary porosity that is critical to the exceptional lubricity of a natural meniscus. Furthermore, since there is no need for manufacturing a mold, the fabrication process is quicker and more economic. More importantly, it can make patient-specific artificial meniscus.

In another embodiment, the present invention relates to the fabrication of PCU/UHMWPE polymeric blends and using FDM 3D printing to fabricate the PCU/UHMWPE polymeric blend structures with porosity. This porosity leads to 46% more bovine serum solution absorbed by 3D printed PCU than compression molded PCU, making the implantable structures of the present invention ideal candidates for artificial meniscus applications that require enhanced lubrication mechanisms.

Other embodiments, the implantable structures of the present invention when subject to rotational oscillating tests, under conditions replicating the knee motion, show the embodiments have 27% less wear depth than molded PCU implants due to retained fluid in its porosity. Thus, 3D printing provides a facile and economic approach to fabricate porous, customizable PCU implants that mimic meniscus lubrication. The fabrication methods can also be applied to a wide range of other biomedical applications such as tissue engineering, where porosity and mechanical strength are desired.

In other embodiments, the present invention provides methods of fabrication of PCU/UHMWPE polymeric blends and using FDM 3D printing to fabricate porous, PCU/UHMWPE polymeric blend structures that can be applied to fabricating soft load-bearing tissues such as an intervertebral disc, meniscus, and articular cartilage to enable native lubrication mechanisms.

In other aspects, the embodiments of the present invention may also be applied to a wide range of other applications where the porosity can change surface properties such as wetting and cell adhesion properties.

In other embodiments, the present invention provides a system and method wherein the elastohydrodynamic, micro-elastohydrodynamic, and importantly "weeping" lubrication, i.e., under dynamic load, the porous, natural meniscus absorbs interstitial synovial fluid with de-pressurization and releases it upon loading, contributing to keeping the opposed surfaces apart and thus reduces friction and wear.

In other embodiments, the present invention provides a system and method of fabricating PCU/UHMWPE structures, such as synovial joints or other anatomical structures. The lubrication mechanisms of the structures combine full fluid film lubrication, elastohydrodynamic, micro-elastohydrodynamic, and more importantly "weeping" lubrication, i.e., under dynamic load. The structures are porous and mimic how natural structures, such as the meniscus, absorbs interstitial synovial fluid with de-pressurization and releases it upon loading, contributing to keeping the opposed surfaces apart and thus reduces friction and wear.

Additional objects and advantages of the invention will be set forth in part in the description which follows, and in part will be obvious from the description, or may be learned by practice of the invention. The objects and advantages of the invention will be realized and attained using the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

FIG. 9C that the wear rates of the indicated structures are similar.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

In one embodiment, the present invention provides the following systems and methods including a first step which concerns the fabrication of blended polymer filaments such as PCU/UHMWPE blended filaments which may be used with a preferred embodiment of the present invention. In one other embodiment, the method fabricates a medical implant having the ability to absorb fluid with de-pressurization and to release fluid upon loading. The method provides a polymeric material and supplies the provided polymeric material to a 3D printing device, and uses said 3D printing device to dispense said polymeric material in a layer-by-layer manner to create said medical implant. During the layer-by-layer dispensing a reduced speed may be used for the bottom and top 1 to 10 layers.

In yet one other embodiment, the method fabricates a medical implant having the ability to absorb interstitial synovial with de-pressurization and to release interstitial synovial upon loading. The method provides a polymeric material and supplies the provided polymeric material to a 3D printing device, and uses said 3D printing device to dispense said polymeric material in a layer-by-layer manner to create said medical implant. During the layer-by-layer dispensing a reduced speed may be used for the bottom and top 1 to 10 layers.

In yet one other embodiment, the method fabricates an implantable meniscus having the ability to absorb interstitial synovial fluid with de-pressurization and to release interstitial synovial fluid upon loading. The method provides a polymeric material and supplies the provided polymeric material to a 3D printing device, and uses said 3D printing device to dispense said polymeric material in a layer-by-layer manner to create said medical implant. During the layer-by-layer dispensing a reduced speed may be used for the bottom and top 1 to 10 layers.

Figure 1:
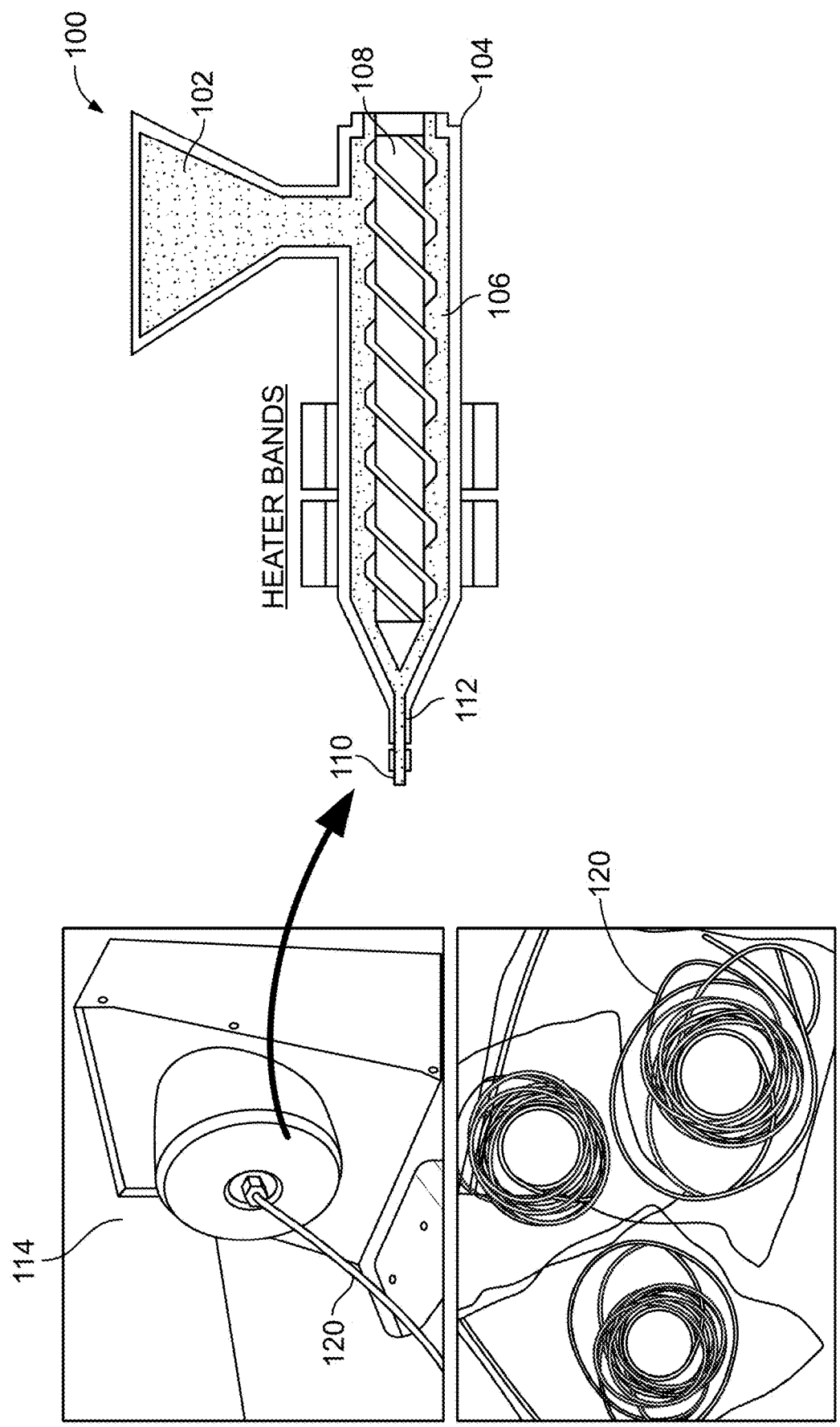
FIG. 1 illustrates a filament maker for an embodiment of the present invention where polymer resin pellets are mixed and extruded into filament.

FIG. 1 illustrates a filament maker 100 for an embodiment of the present invention where polymer resin pellets are mixed and extruded into filament.

In one embodiment, polymeric materials such as PCU (ChronoFlex C 93A) and UHMWPE may be acquired as resin pellets from AdvanSource Biomaterials (Wilmington, Mass., USA) and Ticona Polymers Ltd (Florence, Ky.), respectively. The PCU and UHMWPE resin pellets may be dried in a vacuum oven (Fisher Isotemp Vacuum Oven Model 282) for 10-13 hours at 100° C. to eliminate moisture prior to any processing. The presence of humidity may introduce defects, such as air voids and bubbles in the filament fabrication, which can be carried through the 3D printing. The resin pellets may then be put into the hopper 102 of a single screw filament extruder (for example Filabot EX2 114, Filabot, Barre, Vt.) 104, which may include a heated chamber 106 with a rotating plasticizing/feed screw 108 inside. The pellets go through the chamber 106, and the screw enables mixing and also pushes the blend out through a circular opening 110, extruding the blended filaments 120 as shown in FIG. 1.

In one embodiment, different heating temperatures may be used for fabricating filaments with different UHMWPE wt. % added in PCU. For example, when 5% wt. of UHMWPE is added, the extrusion temperature was set to 183° C. If a concentration of 10 or 15% wt. was used, the extrusion temperature was maintained between 184-186° C. To accelerate the cooling, a small fan may be placed at approximately 50 cm distance from the extruder nozzle 112 as illustrated in FIG. 1. The filaments were maintained in a nitrogen desiccator after fabrication and while not in use.

Figure 2:
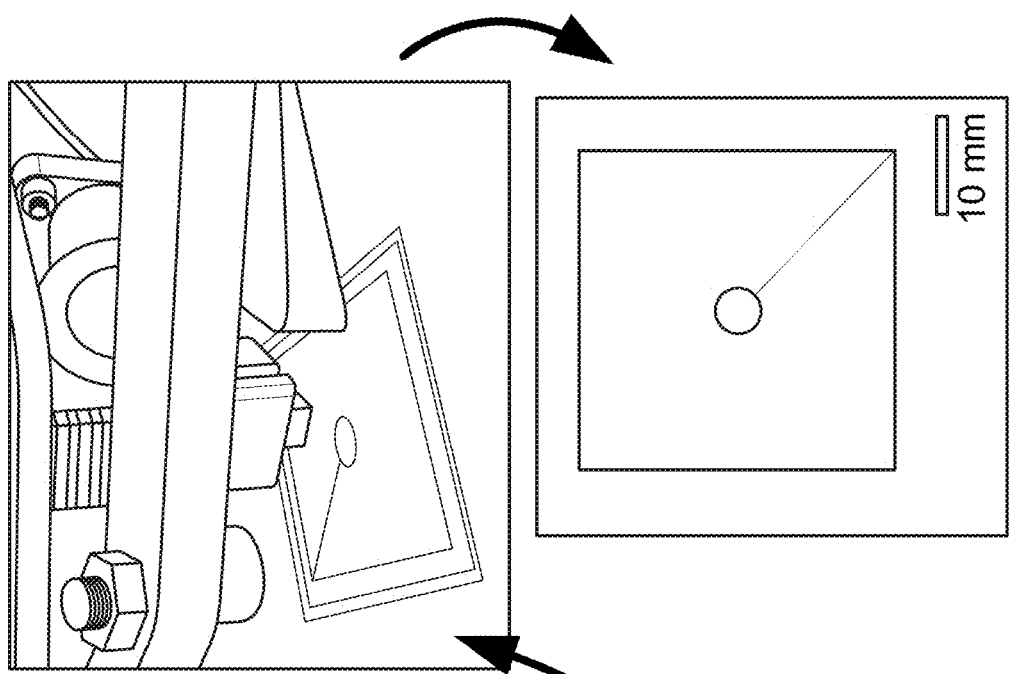
FIG. 2 shows a printing apparatus that may be used with an embodiment of the present invention.
Figure 2:
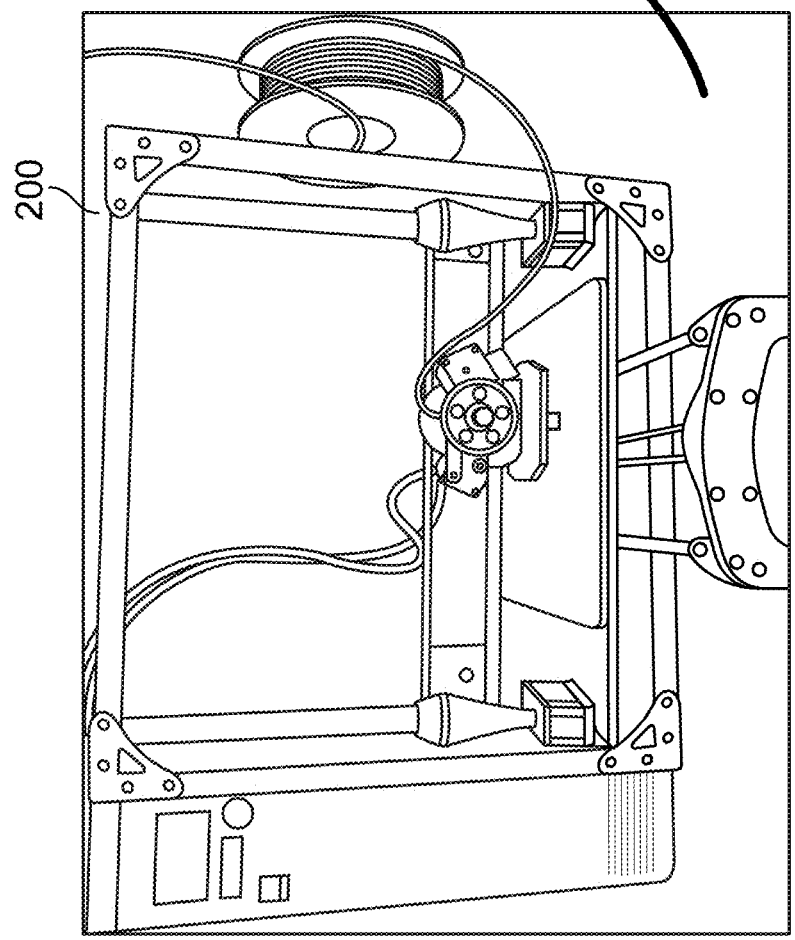

The present invention may also include a second step which includes 3D printing using the PCU/UHMWPE blended filaments. In one embodiment, the fabricated PCU/UHMWPE blended filaments may be used with an FDM 3D printer 200, a Lulzbot TAZ 6 with a FlexyDually V2 print head (both from Aleph Objects, Inc., Loveland, Colo.), customized with a 0.25 mm brass nozzle (E3D, Oxfordshire, United Kingdom) as shown in FIG. 2. In one embodiment, the fabricated PCU/UHMWPE blended filaments may be dispensed at up to 100% infill.

To find a set of 3D printing parameters that produced the best processing performance and quality, an investigation was conducted on a number of structures made in accordance with the present invention. The structures were printed on a polyetherimide print bed at 50° C. and with the nozzle temperature set at 235° C. Print infill density was 100% using a 0.125 mm layer height and following a rectilinear pattern. Speed throughout the print job was 20 mm/s, while a reduced speed of 15 mm/s was maintained for the bottom and top 4 layers to ensure an improved surface finish. In one embodiment, during the layer-by-layer dispensing a reduced speed is used for the bottom and top 1 to 10 layers. In yet one other embodiment, during the layer-by-layer dispensing a reduced speed is used for the bottom and top layers. The FDM structures were designed using Solidworks and measured 32 mm×32 mm×3 mm. Cura, a 3D model to toolpath slicer software for Lulzbot, was used to slice the models and generate the G-code.

Laser scanning confocal microscopy of the surfaces of the structures was performed to compare the friction and wear performance of the 3D printed implantable structures of the present invention with molded structures. FIGS. 3A-3D are Images of surfaces used for friction and wear tests captured with laser scanning microscope. (A) Pure PCU (CF0), (B) PCU with 10 wt. % UHMWPE (CF10), (C) molded PCU (CFm), and (D) molded UHMWPE (UHMWPEm) samples. A laser scanning confocal microscope (LSCM, VK-X260K, Keyence, USA) was used to measure the average surface roughness ($S_a$), and root mean square roughness ($S_q$) of the structures. The average surface roughness ($S_a$) and root mean square roughness ($S_q$) are summarized in Table 1.

TABLE 1

Samples surface roughness and water contact angle

| Sample ID | Filament Surface | | Sample Surface | | Sample WCA (°) |
| --- | --- | --- | --- | --- | --- |
| | $S_a$ (µm) | $S_q$ (µm) | $S_a$ (µm) | $S_q$ (µm) | |
| CF0 | 0.3 ± 0.09 | 0.4 ± 0.1 | 1.5 ± 0.1 | 2.2 ± 0.3 | 82.9 ± 2 |
| CF10 | 1.9 ± 0.7 | 2.2 ± 0.9 | 2.5 ± 0.4 | 4.1 ± 0.4 | 88.8 ± 7 |
| CFm | N/A | N/A | 1.4 ± 0.1 | 1.8 ± 0.1 | 80.4 ± 3 |
| UHMWPEm | N/A | N/A | 1.1 ± 0.1 | 2.1 ± 0.4 | 82.6 ± 3 |

Figures 3A, 3B, 3C, 3D:
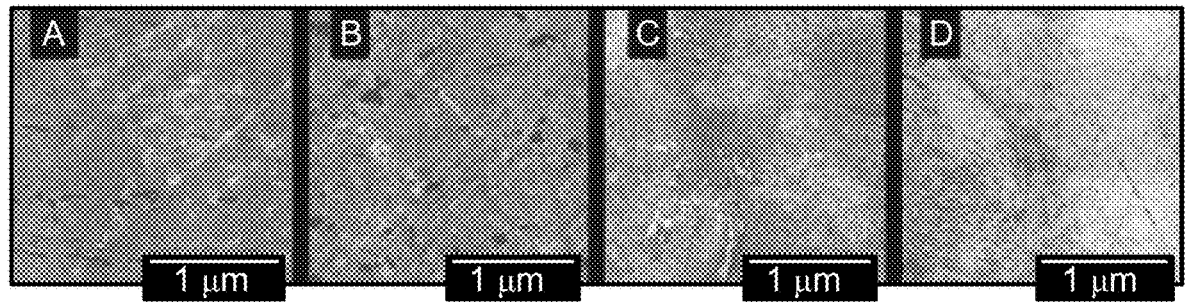
FIGS. 3A, 3B, 3C and 3D are Images of surfaces used for friction and wear tests captured with laser scanning microscope. (A) Pure PCU (CF0), (B) PCU with 10 wt. % UHMWPE (CF10), (C) molded PCU (CFm), and (D) molded UHMWPE (UHMWPEm) samples. 3

It can be seen from Table 1 that the blended 3D printed (CF10) has the highest average surface roughness (2.5±0.4 µm) but within the range of those in natural cartilage (2-5 µm). The 3D printed and molded PCU structures showed comparable and lower average surface roughness (1.5±0.1 µm for CF0 and 1.4±0.1 µm for CFm). The molded UHMWPE had the lowest roughness (1.1±0.1 µm). From FIGS. 3A-3B, directional lines and voids inherent to 3D printing can be seen on 3A (CF0) and 3B (CF10). Some marks are also observed on the molded structures, as illustrated in FIGS. 3C (CFm) and 3D (UHMWPEm), mainly due to the molded surfaces not have been polished. Despite the defects, molded structures still showed lower surface roughness.

A video-based contact angle measurement system (OCA 15 plus, DataPhysics Instruments GmbH, Germany) was used to measure the water contact angles (WCAs) of the structures through the sessile drop method. Three measurements were taken across the surface of each using de-ionized water droplets of 3 µL. An average of the left and the right contact angle was calculated for each of the measurements. The WCAs of all four types of structures are presented in Table 1. No significant differences were found among the WCAs of the structures. Furthermore, all structures have average WCAs less than 90°.

To observe the internal structure of the 3D printed structures, a microtome technique (IsoMet Low-Speed Saw, Buehler, Lake Bluff, Ill.) was used for cutting the structures and scanning electron microscopy (SEM; model XL-30, Phillips/FEI, Hillsboro, Oreg.) was used in order to visualize the cross-sectional area. Structures prepared using microtome cut revealed diverse cross-sectional morphologies among the structures. FIGS. 4A-4H are SEM images of the cross-sectional areas of the samples cut through microtome technique. FIGS. 4A through D represent CF0, CF10, CFm and UHMWPEm, respectively. FIGS. 4E through H follow the same order and show higher magnification images.

Figures 4A, 4B, 4C, 4D:
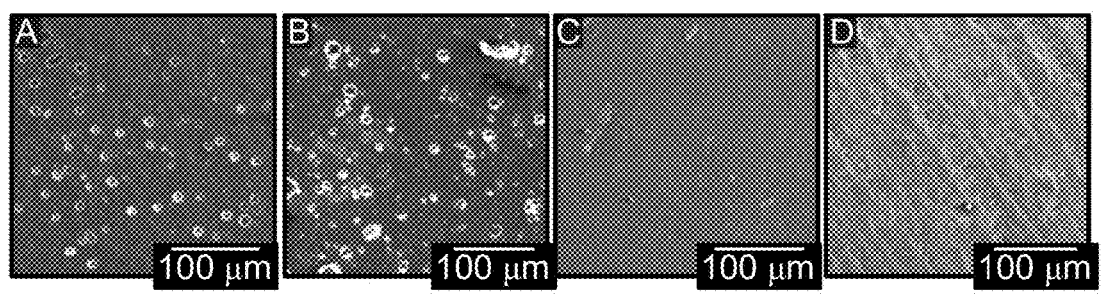
FIGS. 4A, 4B, 4C, 4D, 4E, 4F, 4G and 4H are SEM images of the cross-sectional areas of the samples cut through microtome technique. A through D represent CF0, CF10, CFm and UHMWPEm, respectively. Images E through H follow the same order and show higher magnification images.
Figures 4E, 4F, 4G, 4H:
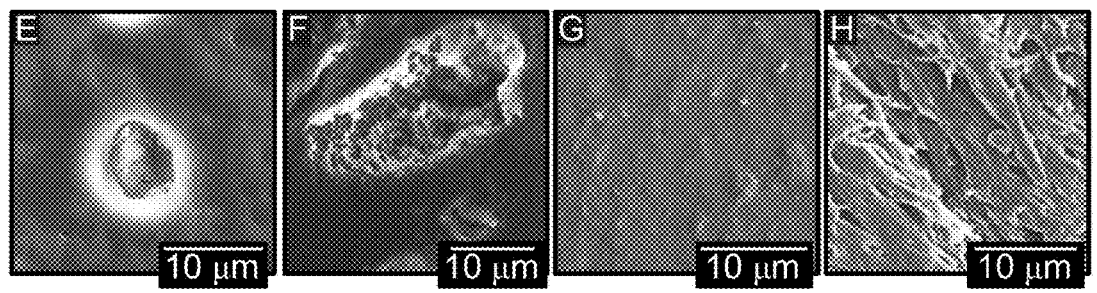

SEM images in FIGS. 4A-4H show porosities on the 3D printed structures (FIGS. 4A and B) and micro/nano-scale roughness was found inside the pores of the CF10 (FIG. 4F). It was noticed that CF10 structures had a higher concentration of pores (FIGS. 4B and F) and that they looked larger than the ones seen on CF0 cross-sectional area, vide FIGS. 4A and E.

Different sections of the cross-sectional area of a set of structures were also observed using the LSCM, which showed surfaces with similar morphology as what was seen on the SEM micrographs. Those measurements considered larger areas at multiple points of each surface, while the SEM was a representative measurement. 13.61% of CF10 cross-sectional area represented pores, while 6.34% of CF0 was pores.

The addition of UHMWPE to a PCU as well as the 3D printing fabrication of the blend increased the amount of porosity as compared to 3D printed pure PCU. In contrast, the molded PCU cross-sectional surfaces showed no pore features. On the other hand, scars from the microtome cut can be seen on the molded UHMWPE cross-sectional area (FIG. 4D). A higher magnification image (FIG. 4H) shows its microstructure, with non-spherical, entangled lamellae, typical of UHMWPE morphology.

Figure 5:
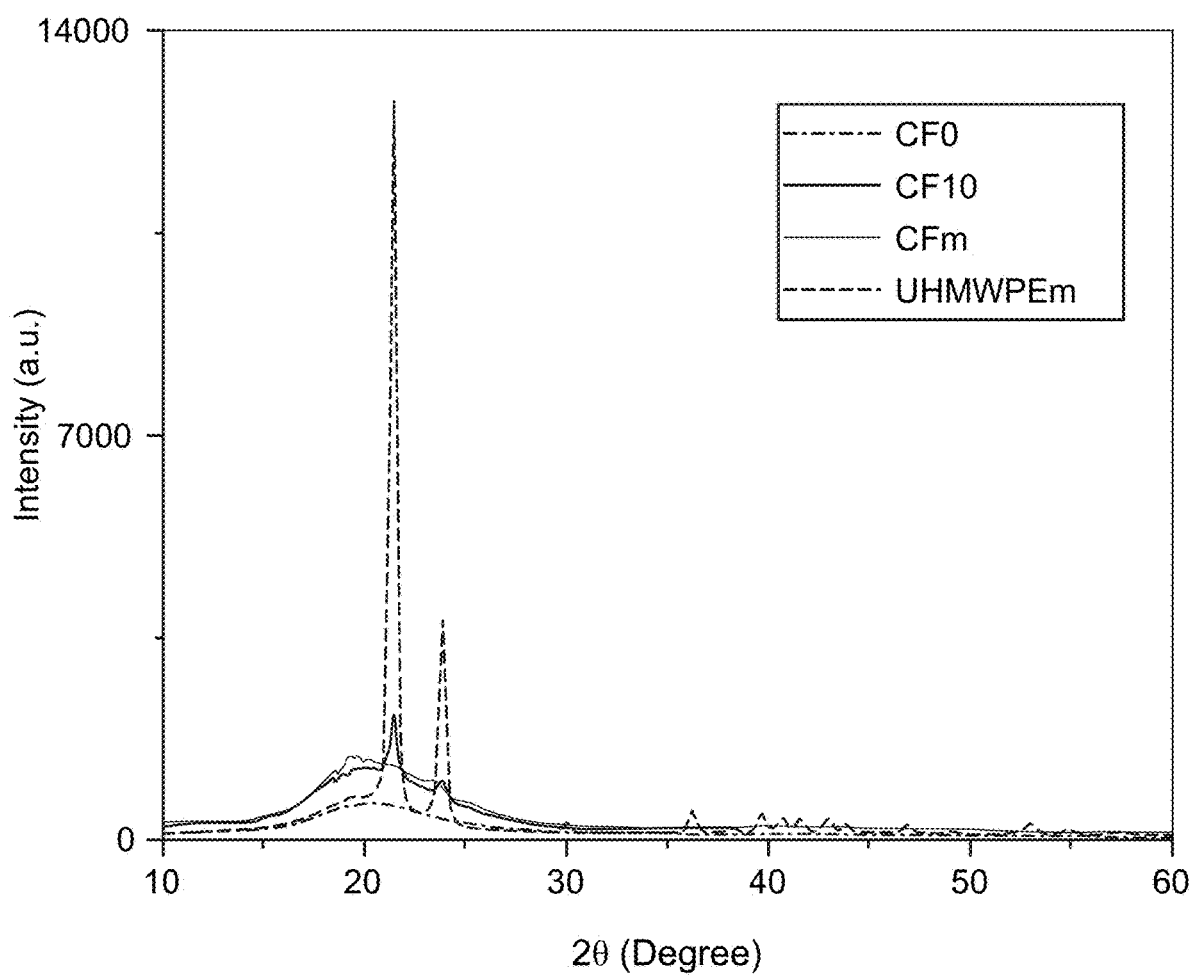
FIG. 5 shows the X-ray diffraction spectrum of blended sample (CF10) showing the influence of adding UHMWPE in PCU with characteristic peaks from the crystallinity pattern of UHMWPE.

X-ray diffraction (XRD) measurements were performed on the structures made in accordance with the present invention to examine the crystallinity after blending and fabrication. These measurements were carried out using a PW3040 X'Pert-MPD (Philips, Holland) diffractometer with Cu K$\alpha$-radiation, $\lambda$=0.15418 nm, in Bragg-Brentano geometry. FIG. 5 shows the XRD spectra of the four types of structures. The crystalline structures of PCU (CF0 and CFm) are consistent regardless of the manufacturing method, i.e., both CF0 and CFm have a broad peak around $2\theta$=20°, which is the characteristic peak of PCU. However, the intensity of the peak for the molded PCU is higher than the 3D printed PCU due to it having more volume of material than the 3D printed that has porosity. On the other hand, UHWMPEm shows two peaks, at $2\theta$=21.5° and 24°, that are consistent with the literature reported UHMWPE crystalline diffraction peaks at these angles. Finally, the CF10 blend had three apparent peaks from both PCU and UHMWPE, around $2\theta$=20°, 21.5° and 24°, but the peak intensities were lower than those of CF0 and UHWMPE separately.

Absorption tests were conducted by immersing structures in a 30 vol. % solution of bovine serum in water, refrigerated at 4-6° C. The structures were dried in a vacuum oven at 100° C. for 10-12 hours prior to the procedure. They were then subject to complete submersion for 24 hours, during which they had their weight checked at 10, 20 and 40 minutes, and every hour for the first 6 hours, followed by checkpoints at 12 and 24 hours. At each inspection, structures were removed from the media, blotted dry, and immediately weighted on a precision balance (GD-503-NTEP, Sartorius, Germany).

Figure 6A:
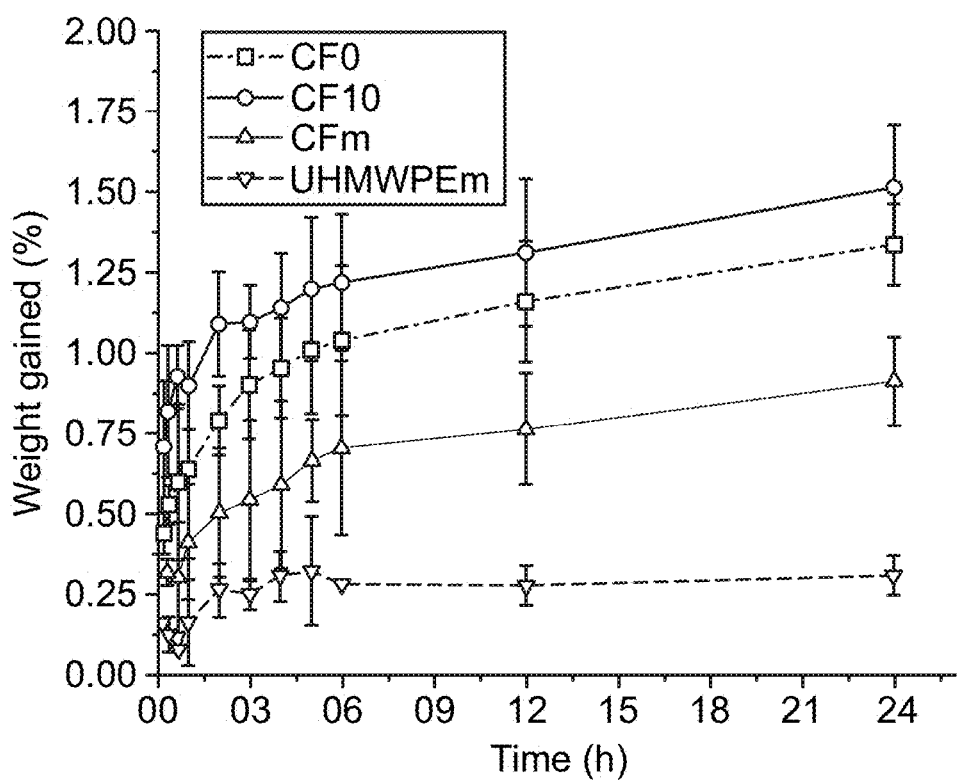
FIG. 6A shows absorption tests results with increasing weight over 24-hours immersion in bovine serum for an embodiment of the present invention.
Figure 6B:
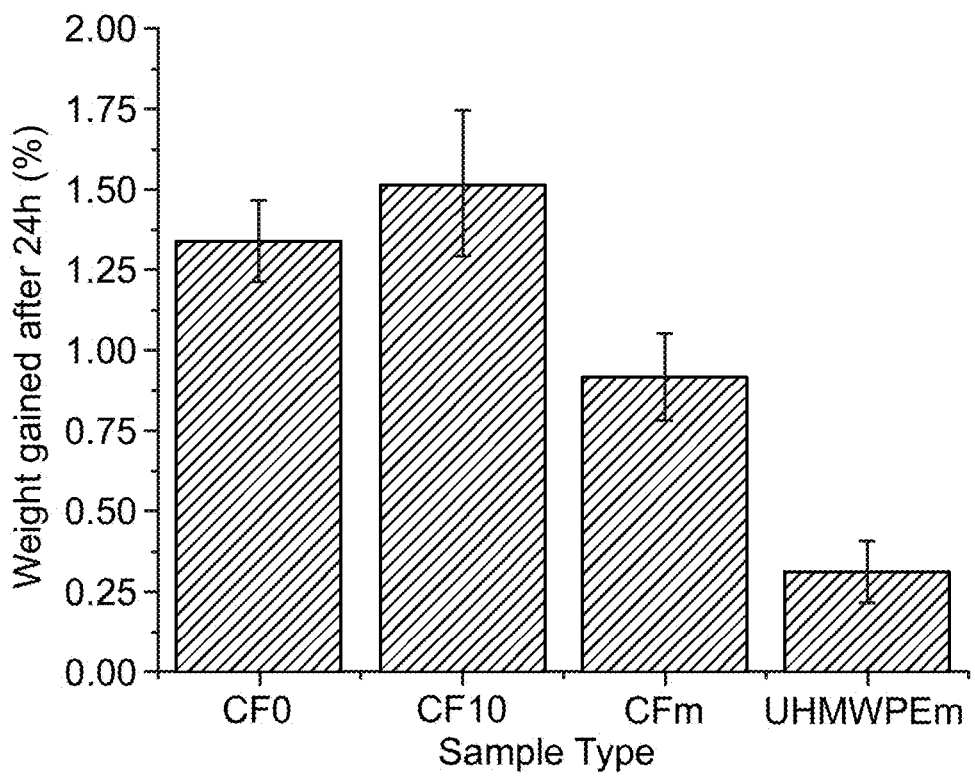
FIG. 6B show average weight gain after total immersion time which shows increasing trend with increasing amount of porosity for an embodiment of the present invention.

FIGS. 6A and 6B show the absorption properties of all four types of structures. The structures showed different absorption properties with that of the CF10 being the highest. The resulting porosity of the 3D printed structures made in accordance with the present invention provide many useful end products of the methods disclosed herein. By depositing the material layer by layer, the FDM 3D printing fabrication method does not produce structures with a solid structure, although the printer was configured to deliver a 100% infill. This resulted in inherent micro-sized voids within the structures that increase the capacity of fluid absorption of the already hydrophilic structures. As can be seen from FIGS. 4B and F, CF10 has the largest amount of porosity, and the micro/nano-scale roughness on the walls of the pores further enhanced its absorption property. FIG. 6A shows the weight continue to increase over time for all PCU structures while the weight of the UHMWPEm stabilized after the first 4 hours of immersion.

In FIG. 6B, the average weight gained after 24 hours by the molded PCU (CFm) is about 0.9% which is in line with the value reported by the manufacturer. It was found that the weight gains due to the fluid absorption of CF10 and CF0 are significantly larger than that of CFm, with CF0 absorbing 46.3% more fluid than its molded version, CFm. CF0 structures also presented an absorption rate that was more than 4 times that of the UHMWPEm. That higher absorption rate, combined with the cushion bearing ability, enables micro-elastohydrodynamic lubrication to take place. These pores play an important role in the bovine serum absorption. By having a porous structure with improved absorption rates, 3D printed structures are closer to mimicking a natural meniscus. Furthermore, porous implants have been shown to increase cell adhesion and stimulate tissue regeneration.

Figure 7:
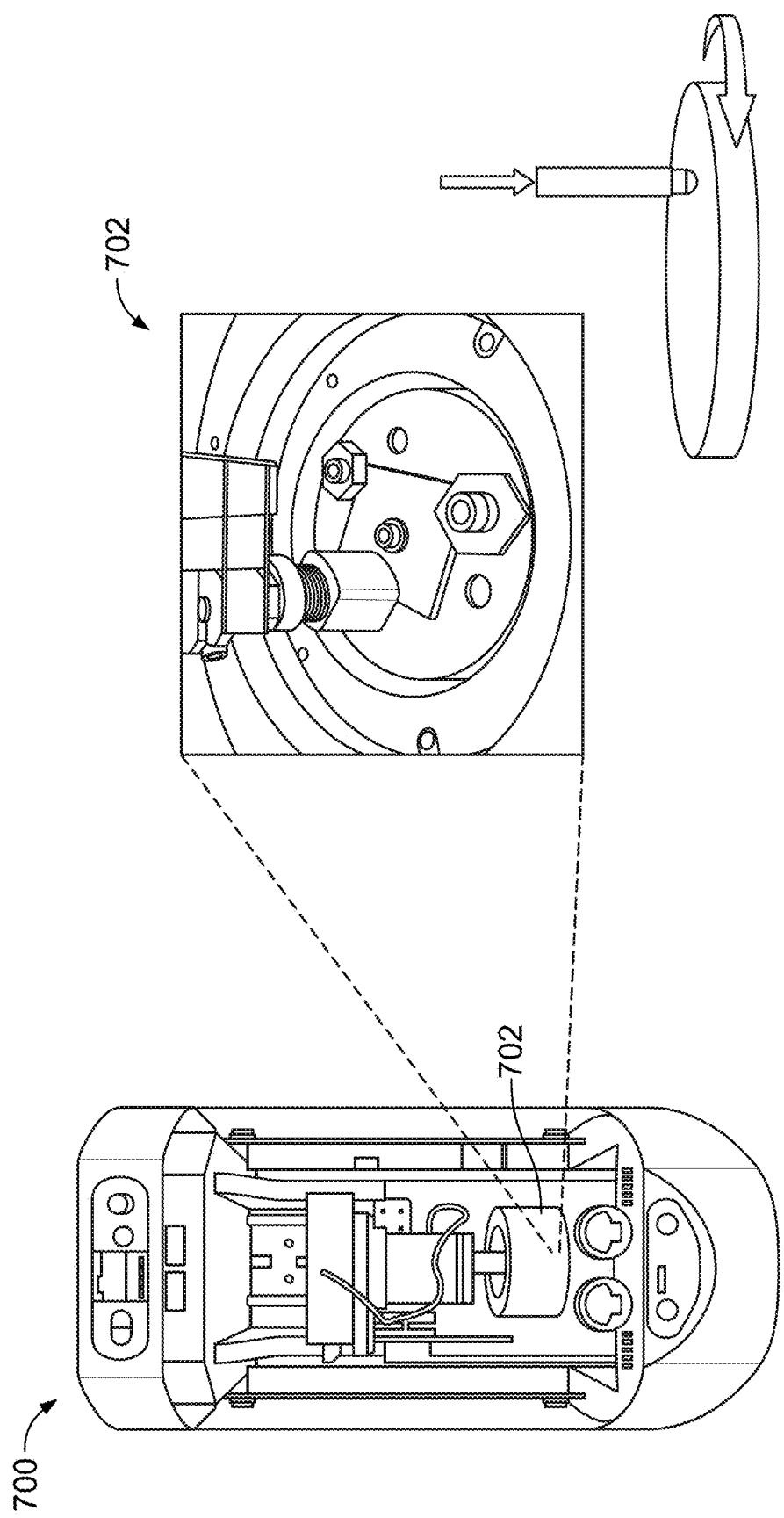
FIG. 7 illustrates a tribological experiment setup used with an embodiment of the present invention.

Tribological testing was performed on the 3D printed structures made in accordance with the present invention. A Universal Mechanical Tester (UMT-2, Bruker Corporation, San Jose, Calif., USA) 700 as illustrated in FIG. 7 was used to perform the tribological tests. The machine measures simultaneously frictional forces and normal loads, and for this experiment, it was equipped with a temperature-controlled chamber, where a custom lubricant and holder were assembled and maintained. Structures were subject to 8-hour long rotational oscillating friction tests, rubbing against a 9.5 mm $Si_3N_4$ ball. A normal load of 11.5 N was applied, which generated a maximum contact pressure of 45.2 MPa on the UHMWPE structures. That is about twice the recommended initial peak Hertzian contact pressure according to ASTM F732 for standard test method for total joint prostheses. The same normal load was applied on the pure PCU and the blended structures, which resulted in a maximum Hertzian contact pressure of 2.4 MPa for the former.

Prior to undergoing tribological experiments, the structures were cleaned according to the cleaning procedure described on Annex 1 of ASTM 2025. The knee joint environment was replicated by testing the immersed in a 30 vol. % solution of bovine serum in water, which was prepared by stirring the solution on a magnetic plate for 5 min at 500 RPM. An oscillation angle between 32.4° and 36° and a speed of approximately 7.33 mm/sec were maintained, while the temperature chamber preserved the environment at 37° C. Table 2 shows the details for the tribological tests, while FIG. 7 shows the UMT-2 Universal Mechanical Tester 700 in a detailed image of the experimental setup, with a 3D printed structure clamped in a sample holder 702.

TABLE 2

Tribological experiment details

| Material | PCU | UHMWPE |
|---|---|---|
| Loan (N) | | 11.5 |
| Max. Hertzian Contact Pressure (MPa) | 2.4 | 45.2 |
| Max. Hertzian Contact Pressure (MPa) Based on ASTM F732 | | 29-36 |
| Rotational Speed (RPM) | | 10 |

TABLE 2-continued

Tribological experiment details

| Material | PCU | UHMWPE |
|---|---|---|
| Equivalent Linear Speed (mm/sec) | | 7.33 |
| Oscillation angle (°) | | 36 |
| Temperature (° C.) | | 37 |

The sliding distance was calculated from the radius and oscillation angle and then used with the applied normal load of 11.5 N and a linear speed of 7.33 mm/sec to calculate the wear rate.

Figure 8A:
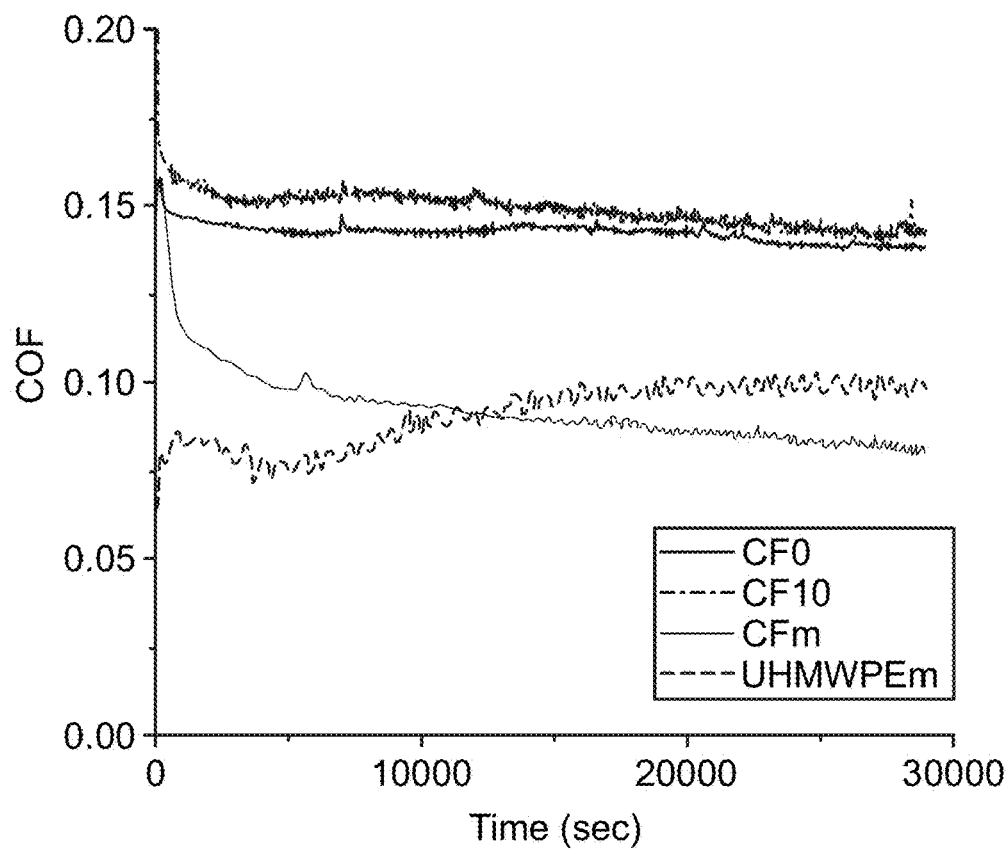
FIGS. 8A and 8B show COF of all four types of samples. (A) COF as a function of test duration. 3D printed samples showed higher COF but more steady curves. COF of CFm showed a decreasing trend. (B) Average COF for all samples. 3D printed samples showed higher COF than the molded samples.
Figure 8B:
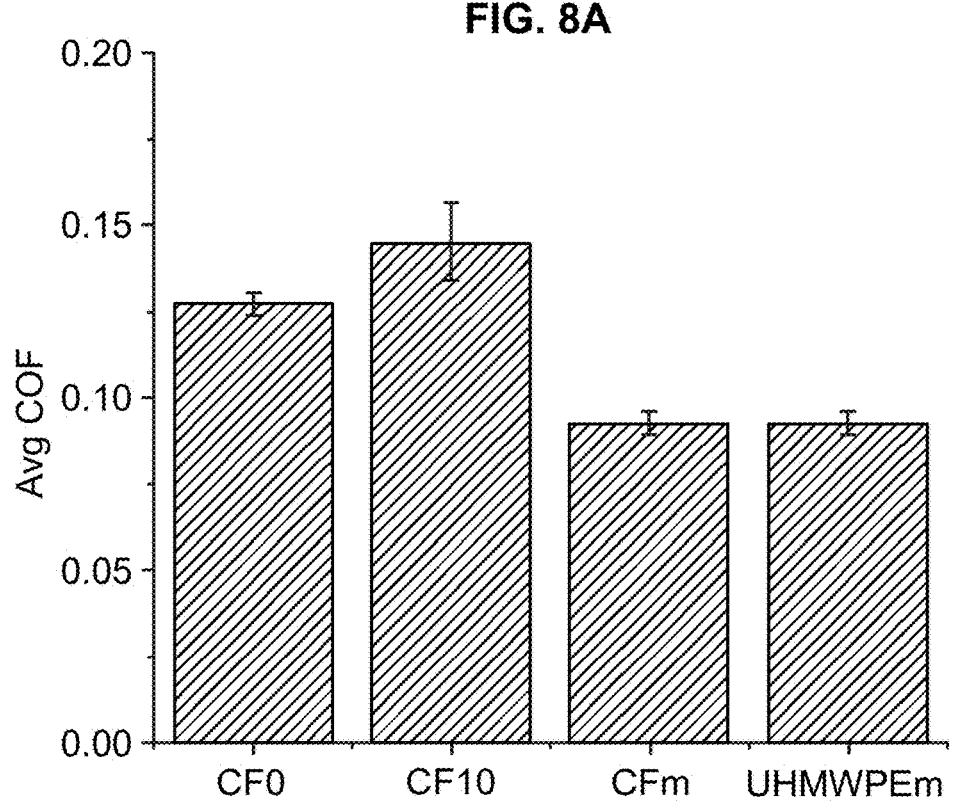
Figure 9A:
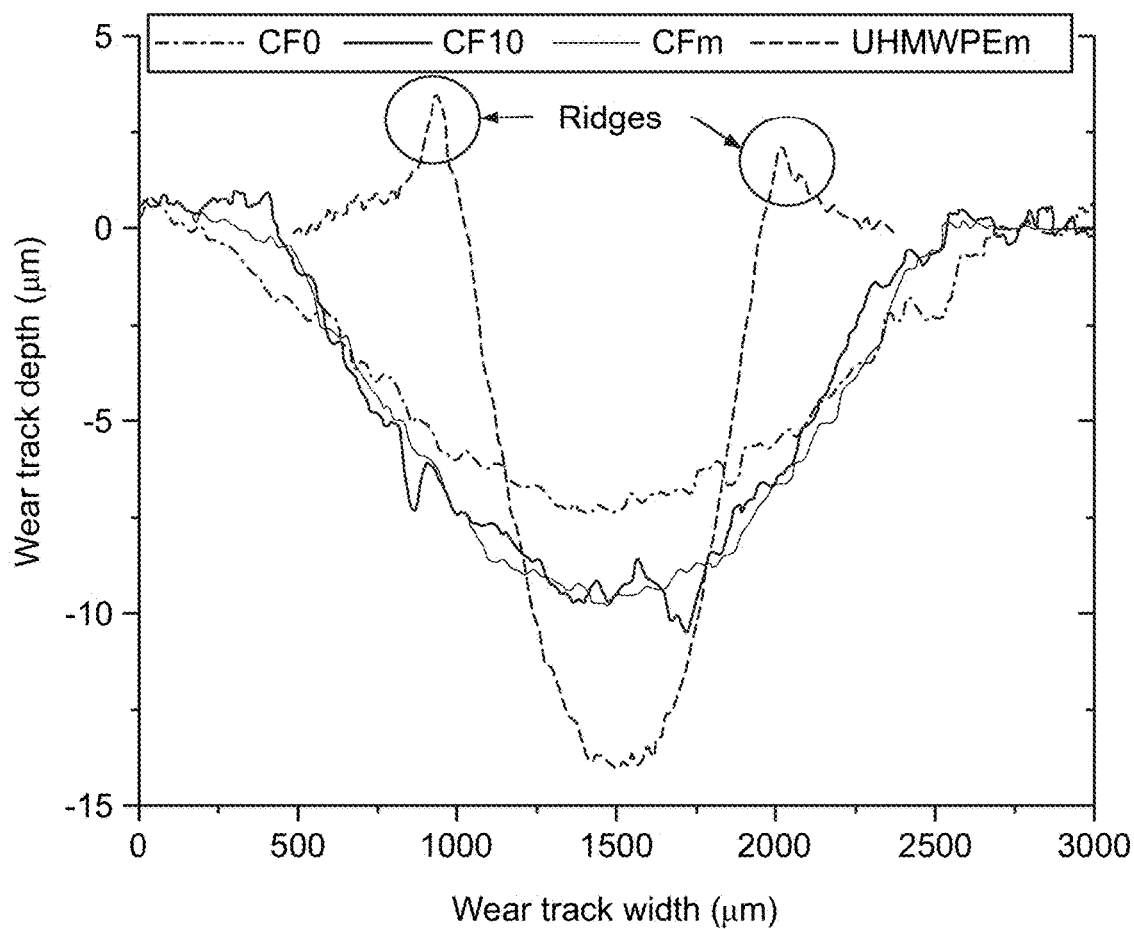
FIG. 9A shows the average wear track profiles showing the disparities between molded UHMWPE and PCU structures.

FIG. 8A shows the average COF changes of the four types of structures over the test duration and FIG. 8B summarizes the COF average of all structures and all tests over the entire test period. The COF of the 3D printed structures are similar (FIG. 8A), both presenting a decreasing trend after the first 15,000 seconds possibly due to gradual bovine serum solution absorption, but overall in a curve that is stable over time and within the range cited by published literature. They also resulted in greater average COF, which may be explained by the higher surface roughness of the 3D printed structures. The COF of molded PCU tends to decrease and that behavior is observed throughout the entire test. However, UHMWPEm yields a COF that increases at the beginning and then stabilizes around halfway of the testing. The COF of UHMWPEm trend can be explained by the shape of its wear track profile. The narrower and deeper profile of UHMWPEm, as shown in FIG. 9A, indicates that the ball had to slide with a larger contact area, resulting in an increase in COF, unlike the other structures. In addition, UHMWPEm has the lowest absorption rate of bovine serum solution, which causes the surface to be less lubricated by the bovine serum solution at the beginning of the test.

Figure 9B:
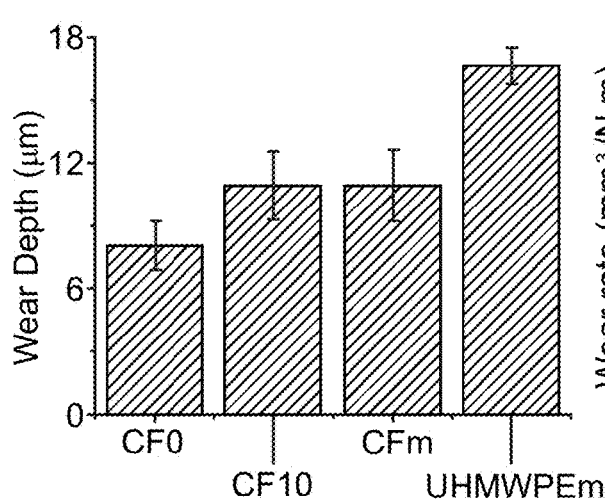
FIG. 9B shows the wear depths of CF0 is much smaller than that of UHMWPEm wear track.
Figure 9C:
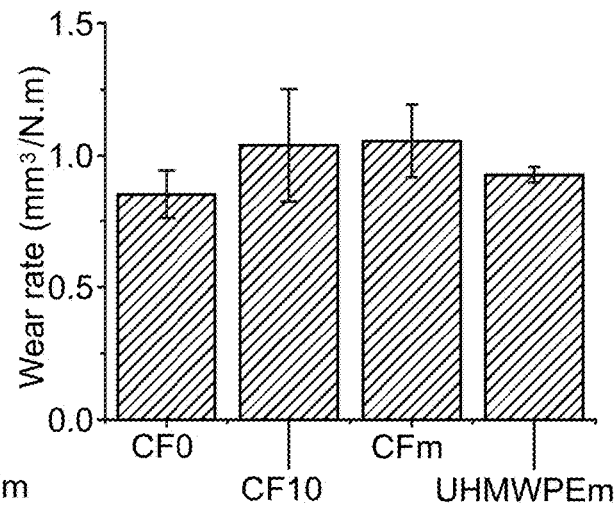
Figure 10A:
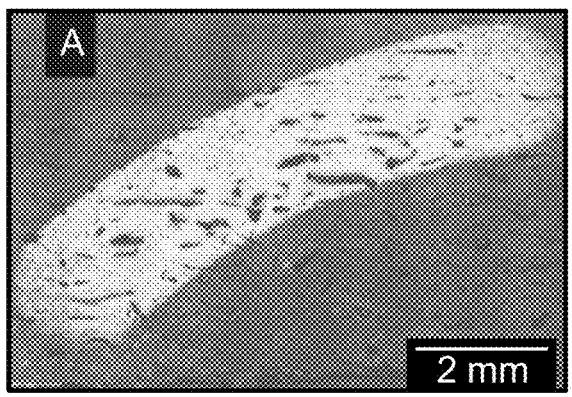
FIGS. 10A-10D show optical images of the wear tracks from laser scanning microscope. (A) CF0, (B) CF10, (C) CFm, and (D) UHMWPEm.
Figure 10B:
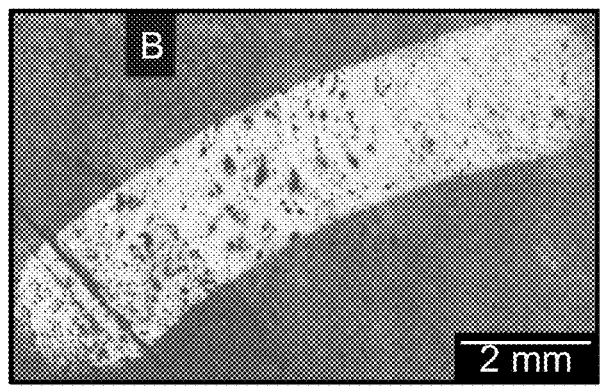
Figure 10C:
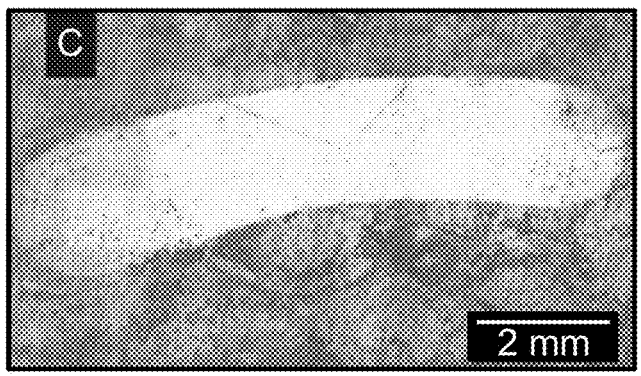
Figure 10D:
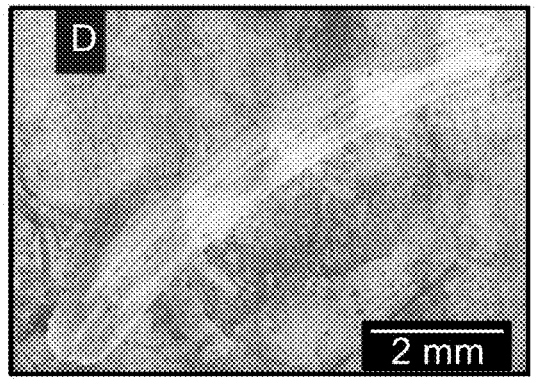

The wear track was quantified with Keyence Multi-File Analyzer software by comparing the wear track profiles as shown in FIG. 9A. The wear tracks of all PCU structures have a similar appearance, as seen on FIG. 10. Their wear track profiles also have analogous shape, with the same width, but different depths, as shown in FIG. 9A. The normalized wear rate, FIG. 9C was calculated from the wear track cross-sectional area found with the LSCM. Although no statistically significant difference was found among the wear rate results, the depth and shape of the profiles are notably distinct. The deepest profile was found to be from UHMWPEm, and the shallowest, CF0 (FIG. 9B). In general, the 3D printed structures presented lower wear track depth. CF0 structures had an average of 27% lower wear depth compared to molded PCU. CF0 and CF10 wear depths were 52% and 34% lower, respectively, than that of UHMWPEm. Furthermore, the wear track profile of UHMWPEm was narrower than all PCU structures, and formed ridges that commonly cause plastic deformation, pitting and fatigue wear. Those sharp ridges (FIG. 9A) may cause local stress concentration and eventually break into wear particles, potentially accelerating the wear process.

Published works have shown that PCU not only yields a lower wear rate compared to UHMWPE, but also, in general, generates wear particles that are larger, and that is relatively less harmful to the joint. Although phagocytosis of wear debris is size dependent, a high concentration of submicron-sized particles induces significant level of secretion of bone resorbing factors. Since the printed PCU (CF0) had a lower wear depth and smoother wear track profile without sharp ridges, the volume of the wear debris would be less than UHMWPE in the long run. Hence, possible risks of adverse biological responses from the wear debris of CF0 are expected to be less concerning compared to those of UHMWPE.

The fabrication methods of the various embodiments of the present invention have proven to be of considerable importance: 3D printed PCU structures resulted in 27% lower wear-track depth compared to molded PCU structures which is achieved by the enhanced lubrication behavior through the porosity of the 3D printed structures. As in natural menisci, the porous structure absorbs and releases synovial fluid with an applied load maintaining the separation between the opposite rubbing surfaces.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. A method for fabricating a medical implant having the ability to absorb fluid with de-pressurization and to release fluid upon loading, the method comprising:
   (a) providing a polymeric material wherein said polymeric material is a blend of polycarbonate-urethane and ultra-high molecular weight polyethylene (PCU/UHMWPE);
   (b) supplying said polymeric material to a 3D printing device; and
   (c) using said 3D printing device to dispense said polymeric material in a layer-by-layer manner to create said medical implant.

2. The method of claim 1 wherein said PCU/UHMWPE is in the form of a filament.

3. The method of claim 1 wherein said polymeric material is dispensed at up to 100% infill.

4. A method for fabricating a medical implant having the ability to absorb interstitial synovial fluid with de-pressurization and to release interstitial synovial fluid upon loading, the method comprising:
   (a) providing a polymeric material wherein said polymeric material is a blend of polycarbonate-urethane and ultra-high molecular weight polyethylene (PCU/UHMWPE);
   (b) supplying said polymeric material to a 3D printing device; and
   (c) using said 3D printer to dispense said polymeric material in a layer-by-layer manner to create said medical implant.

5. The method of claim 4 wherein said PCU/UHMWPE is in the form of a filament.

6. The method of claim 4 wherein said polymeric material is dispensed at up to 100% infill.

7. A method for fabricating an implantable meniscus having the ability to absorb interstitial synovial fluid with de-pressurization and to release interstitial synovial fluid upon loading, the method comprising:
   (a) providing a polymeric material wherein said polymeric material is a blend of polycarbonate-urethane and ultra-high molecular weight polyethylene (PCU/UHMWPE);
   (b) supplying said polymeric material to a 3D printing device; and (c) using said 3D printer to dispense said polymeric material in a layer-by-layer manner to create said medical implant.

8. The method of claim 7 wherein said PCU/UHMWPE is in the form of a filament.

9. The method of claim 7 wherein said polymeric material is dispensed at up to 100% infill.

10. The method of claim 1 wherein during the layer-by-layer dispensing a reduced speed is used for the bottom and top layers.

11. The method of claim 10 wherein during the layer-by-layer dispensing a reduced speed is used for the bottom and top 1 to 10 layers.

12. The method of claim 4 wherein during the layer-by-layer dispensing a reduced speed is used for the bottom and top layers.

13. The method of claim 12 wherein during the layer-by-layer dispensing a reduced speed is used for the bottom and top 1 to 10 layers.

14. The method of claim 7 wherein during the layer-by-layer dispensing a reduced speed is used for the bottom and top layers.

15. The method of claim 14 wherein during the layer-by-layer dispensing a reduced speed is used for the bottom and top 1 to 10 layers.

\* \* \* \* \*